United States Patent [19]

Anderson

[11] Patent Number: 4,623,658
[45] Date of Patent: Nov. 18, 1986

[54] PESTICIDAL BENZOYLUREA COMPOUNDS

[75] Inventor: Martin Anderson, Whitstable, England

[73] Assignee: Shell Oil Company, Houston, Tex.

[21] Appl. No.: 825,172

[22] Filed: Feb. 3, 1986

Related U.S. Application Data

[63] Continuation-in-part of Ser. No. 719,791, Apr. 4, 1985, and Ser. No. 763,584, Aug. 8, 1985, abandoned.

[30] Foreign Application Priority Data

| Apr. 10, 1984 [GB] | United Kingdom | 8409240 |
| Aug. 17, 1984 [GB] | United Kingdom | 8420930 |
| Oct. 4, 1985 [GB] | United Kingdom | 8524545 |

[51] Int. Cl.<sup>4</sup> ............... C07C 145/04; A01N 47/34
[52] U.S. Cl. ............... 514/482; 546/231; 548/542; 558/248; 558/415; 560/13; 560/16; 564/40; 564/41; 564/42; 514/331; 514/424; 514/512; 514/522; 514/534; 514/593; 514/514
[58] Field of Search ............... 560/13, 16; 564/40, 564/42, 41; 546/231; 548/542; 514/331, 424, 482, 512, 522, 534, 593, 514; 558/248, 415

[56] References Cited

U.S. PATENT DOCUMENTS

| 3,992,553 | 11/1976 | Sirrenberg | 564/44 |
| 4,005,223 | 1/1977 | Sirrenberg | 564/44 |
| 4,013,717 | 3/1977 | Wellinga | 564/44 |
| 4,041,177 | 8/1977 | Sirrenberg | 564/44 |
| 4,068,002 | 1/1978 | Sirrenberg | 564/44 |
| 4,508,734 | 4/1985 | Lange | 564/44 |
| 4,529,819 | 7/1985 | Clifford | 564/44 |

FOREIGN PATENT DOCUMENTS

| 57888 | 8/1982 | European Pat. Off. | 564/44 |
| 74074 | 3/1983 | European Pat. Off. | 564/44 |
| 57-2258 | 1/1982 | Japan | 564/44 |
| 57-2259 | 1/1982 | Japan | 564/44 |

*Primary Examiner*—Michael L. Shippen

[57] ABSTRACT

Pesticidal benzoylurea compounds of the formula:

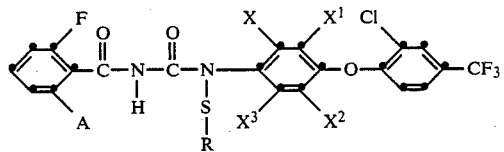

wherein R represents a moiety $-C(O)OR^1$ or $-NR^2R^3$, and the meanings of each of the other symbols is described in the specification.

15 Claims, No Drawings

PESTICIDAL BENZOYLUREA COMPOUNDS

This application is a continuation-in-part of application Ser. No. 719,791, filed 4/4/85, and of application Ser. No. 763,584 filed 8/8/85, now abandoned.

DESCRIPTION OF THE INVENTION

It has been found that useful insecticidal and acaricidal properties are shown by compounds of the formula:

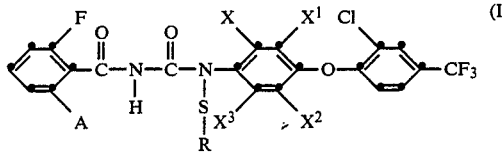

wherein A is fluorine or chlorine, X, $X^1$, $X^2$ and $X^3$ each is hydrogen or fluorine, R is a moiety $-C(O)OR^1$, or $-NR^2R^3$, in which $R^1$ and $R^2$ each is optionally substituted alkyl, optionally substituted cycloalkyl or optionally substituted phenyl, $R^3$ is optionally substituted alkyl, optionally substituted cycloalkyl or optionally substituted phenyl, or is a moiety $-C(O)R^4$, $-C(O)OR^4$ or $-SO_2R^4$ wherein $R^4$ is optionally substituted alkyl, optionally substituted cycloalkyl or optionally substituted phenyl, or $R^2$ and $R^3$ together is optionally substituted alkylene of four or five carbon atoms, in each case the optional substituents on alkyl, cycloalkyl and alkylene being selected from halogen, alkoxy, alkoxycarbonyl, haloalkoxycarbonyl, alkylcarbonyl, haloalkylcarbonyl, alkylsulphonyl and haloalkylsulphonyl, and the optional substituents on phenyl being selected from these substituents and also alkyl, haloalkyl, cyano and nitro, wherein each alkyl and haloalkyl group contains from one to six carbon atoms, especially from one to four carbon atoms. A preferred alkyl group is methyl and a preferred haloalkyl group is trifluoromethyl. Each cycloalkyl group suitably contains from three to six carbon atoms. Preferably, A is fluorine. Preferably, each of $R^1$, $R^2$, $R^3$ and $R^4$, when present, represents unsubstituted alkyl, preferably of up to six carbon atoms.

Preferably R represents a group of the formula $-NR^2R^3$. Preferably $R^2$ is alkyl and $R^3$ is alkyl substituted by alkoxycarbonyl of up to six carbon atoms in the alkyl moiety, or is a group of the formula $-C(O)OR^4$, $-SO_2R^4$, or $-C(O)R^4$ wherein $R^4$ is alkyl.

Especially preferred groups R are those of the formula $-N(R^2)C(O)OR^4$ in which each of $R^2$ and $R^4$ is unsubstituted alkyl of up to six carbon atoms.

The invention also provides a process for the preparation of compounds of Formula I, which comprises treating a compound of the formula

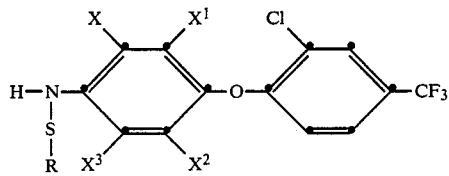

with a compound of the formula:

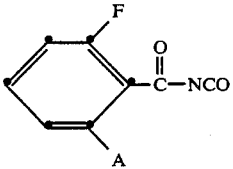

The reaction is suitably carried out in the presence of a solvent. Suitable solvents are aromatic solvents such as benzene, toluene, xylene, or chlorobenzene, hydrocarbons such as petroleum fractions, chlorinated hydrocarbons such as chloroform, methylene chloride or dichloroethane, and ethers such as diethylether, dibutylether, or dioxan. Mixtures of solvents are also suitable.

Preferably the reaction is carried out at a temperature from 0° to 100° C., suitably ambient temperature. Preferably the molar ratio of isocyanate to amine is from 1:1 to 2:1. Preferably the reaction is carried out under anhydrous conditions.

The compounds of Formula II are themselves novel and constitute a further aspect of the invention. They may be prepared by treating a compound of the formula

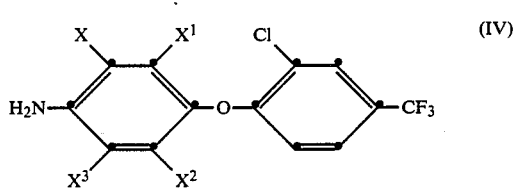

with a compound of the formula

Hal—S—R    (V)

in which Hal represents halogen, especially chlorine. The reaction is preferably carried out in the presence of an inert solvent, for example a hydrocarbon or chlorinated hydrocarbon, and the reaction temperature is preferably in the range of from −30° to +30° C., preferably −10° to −10° C. The reaction is suitably carried out in the presence of a base, for example an amine such as triethylamine.

Compounds of Formula IV can be prepared by treating a compound of the formula

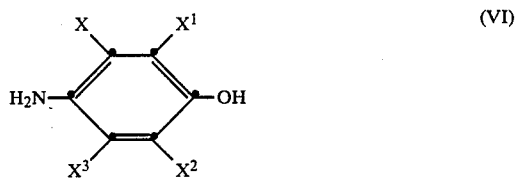

with a compound of the formula

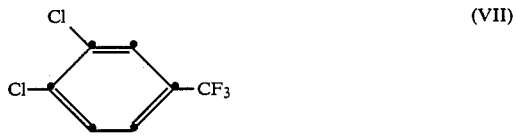

The reaction between the compounds of formulae VI and VII is preferably carried out in the presence of an inert solvent, for example a polar aprotic solvent such as dimethylsulphoxide or dimethylformamide, in the presence of a base, for example an alkali metal hydroxide, alkoxide or carbonate, or an organic base such as pyridine or triethylamine. The reaction temperature is suitably in the range of from 0° C. to 150° C., preferably 30° C. to 100° C.

The compounds of Formula I exhibit pesticidal, for example insecticidal and acaricidal, activity. Accordingly the invention also provides a pesticidal composition comprising a compound of Formula I together with a carrier.

The invention further provides a method of combating pests at a locus, which comprises applying to the locus a pesticidal compound or composition according to the invention. The pests may be insects or acarids, especially mites. The locus may be a crop area susceptible to infestation by acarids.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides—i.e., horticulturally acceptable adjuvants—are suitable.

Suitable solid carriers are natural and synthetic clays and silicates, for example, natural silicas such as diatomaceous earths; magnesium silicates, for example talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25–75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–15% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3–7% by weight of a blend of surfactants, which act as wetting, dispersing, suspending and binding agents, and 1–3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.0001% by weight to as much as about 95% by weight of a compound of the invention as the active ingredient.

The compositions of the invention may also contain other ingredients, for example, other compounds possessing pesticidal, especially insecticidal, acaricidal or fungicidal properties, as are appropriate to the intended purpose.

The method of applying a compound of the invention to control pests comprises applying the compound, ordinarily in a composition of one of the aforementioned types, to a locus or area to be protected from the insects, such as the foliage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected—i.e., the dosage which the insect contacts—is of the order of 0.001 to 0.5% based on the total weight of the formulation, though under some circumstances the effective concentration will be as little as 0.0001% or as much as 2%, on the same basis.

The following Examples illustrate the invention and are drawn to the subgenus of Formula I wherein all of X, $X^1$, $X^2$, and $X^3$ are hydrogen; Examples 1 to 3 illustrate the preparation of intermediates of Formula II, while Examples 4 to 6 illustrate the preparation of compounds of Formula I. In each case, the identity of the product was confirmed by appropriate elemental and spectral analyses.

EXAMPLE 1

Propyl N-[[[4-[2-chloro-4-(trifluoromethyl)phenoxy]phenyl]amino]thio]-N-methylcarbamate (1)

A solution of 3.7 g of N-chlorosulphenyl-N-methylcarbamate in 10 ml of dry methylene chloride was added over 20 minutes to a stirred solution of 6.3 g of 4-[2-chloro-4-(trifluoromethyl)phenoxy]aniline in 25 ml of the same solvent containing 2.5 g of triethylamine. The reaction mixture temperature was kept at 0°–5° C. by means of an ice bath until the addition was completed, and was then allowed to rise to ambient temperature over 2.0 hours. The solvent was removed under reduced pressure and the residue was suspended in 200 ml of diethyl ether and washed three times with water. The resulting ether solution was dried (MgSO$_4$) and the solvent was evaporated. The residue was purified by rapid chromatography on silica gel using methylene chloride as eluent. Crystallisation from diethyl ether/light petroleum gave 1, as pale buff-coloured crystals (m.p.: 61°–64° C.).

EXAMPLE 2

N-[[[4-[2-chloro-4-(trifluoromethyl)phenoxy]phenyl]amino]thio]-N-ethylmethanesulphonamide (2)

A solution of 2.6 g of sulphur dichloride in 15 ml of dry diethyl ether was added over 10 minutes to a stirred solution of 3.1 g of N-ethylmethanesulphonamide in 15 ml of the same solvent, keeping the temperature between 10°–15° by means of external cooling. A solution of 2.0 g of dry pyridine in 15 ml of dry diethyl ether was then added over 15 minutes at the same temperature and the reaction mixture was allowed to warm to room temperature over 1 hour. The resulting suspension was added over 5 minutes to a solution of 7.2 g of 4-[2-chloro-4-(trifluoromethyl)phenoxy]aniline (1A) in 75 ml of dry diethyl ether containing 2.0 g of pyridine, keeping the temperature of the mixture between 5°–10° C. After stirring at 10°–15° for 1 hour, the reaction mixture was washed three times with water, the ether layer was separated, dried (MgSO$_4$), and the solvent was evaporated under reduced pressure. The residue was purified by chromatography on silica gel using diethyl ether as eluent, to give 2, as a buff solid m.p.: 98°–101° C.

EXAMPLE 3

O-Methyl-S[[4-[2-chloro-4-(trifluoromethyl)phenoxy]phenyl]amino]thiocarbonate (3)

A solution of 4.2 g of methoxycarbonylsulphenyl chloride in 5 ml of dry methylene chloride was added over 20 minutes to a stirred solution of 8.6 of 1A in 50 ml of the same solvent containing 6.0 ml of triethylamine, keeping the temperature of the mixture below 0° C. After the addition was complete the stirred reaction mixture was allowed to warm to room temperature over 1.0 hour. The solvent was then evaporated under reduced pressure, the residue was suspended in 180 ml of diethyl ether and washed with water. The extract was dried (MgSO$_4$) and the solvent was evaporated. The residue was purified by chromatography on silica gel using diethyl ether/petroleum ether as eluent. Recrystallisation from the same solvent gave 3, as colourless crystals, m.p.: 71°–72° C.

EXAMPLE 4

Propyl 4-[4-[2-chloro-4-(trifluoromethyl)phenoxy]phenyl]-7-(2,6-difluorophenyl)-2-methyl-5,7-dioxa-3-thia-2,4,6-triazaheptanoate (4)

A solution of 2.4 g of 2,6-difluorobenzoyl isocyanate in 10 ml of dry toluene was added, with stirring, to a solution of 5.2 g of 1 in 40 ml of the same solvent and the resulting solution was stirred at room temperature for 3 hours. The reaction mixture was then diluted with 50 ml of dry light petroleum (b.p.: 40°–60° C.) and stored at −5°–0° C. overnight.

The resulting mixture was filtered, and the collected solid product was washed with light petroluem. Recrystallisation from diethyl ether/light petroleum gave 4 as colourless crystals, m.p.: 96°–98° C.

EXAMPLE 5

N-[[[4-[2-chloro-4-(trifluoromethyl)-phenoxy]phenyl][[(N-ethyl-N-methanesulphonyl)amino]thio]amino]carbonyl]-2,6-difluorobenzamide (5)

A solution of 2.0 g of 2,6-difluorobenzoyl isocyanate in 10 ml of dry diethyl ether was added rapidly to a stirred solution of 4.4 g of 2 in 15 ml of the same solvent at room temperature. After stirring for 4 hours, 10 ml of light petroluem (b.p.: 40°–60° C.) was added, the resulting mixture was filtered, and the collected solid was washed with diethyl ether/light petroleum. Recrystallisation from diethyl ether/light petroleum gave 5, as colourless crystals, m.p.: 149°–151° C.

EXAMPLE 6

Methyl-3-[4-[2-chloro-4-(trifluoromethyl)phenoxy]-phenyl]-6-(2,6-difluorophenyl)-4,6-dioxo-2-thia-3,5-diazahexanoate (6)

A solution of 2.0 g of 2,6difluorobenzoyl isocyanate in 10 ml of dry toluene was added to a stirred solution of 3.8 g of 3 in 30 ml of the same solvent. The mixture was stirred at room temperature for 3 hours. It was then diluted with an equal volume of petroleum ether and cooled in ice-water. After 1 hour, the mixture was cooled to −70° C. for 10 minutes, and the resulting crop of crystals was filtered off, washed with petroleum ether, and dried. Recrystallisation from petroleum ether gave 6, m.p.: 108°–109° C.

EXAMPLES 7 TO 18

By methods analogous to these described in the previous Examples, further compounds of the following formula were prepared, the identity of the moiety R and the melting point of the product being given in each case in Table I.

TABLE I

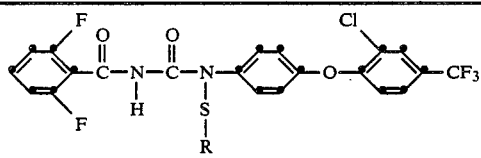

| Example No. | R | Melting Point (°C.) |
|---|---|---|
| 7 | —N(CH₃)C(O)O—CH₃ | 96–100 |
| 8 | —N(CH₃)C(O)O—(n-C₅H₁₁) | 69–71 |
| 9 | —N(C₂H₅)C(O)O—C₂H₅ | 82–85 |
| 10 | —N(t-C₄H₉)C(O)O—CH₃ | 82–85 |
| 11 | —N(t-C₄H₉)C(O)O—C₂H₅ | 110–113 |
| 12 | —N(n-C₄H₉)SO₂CH₃ | 142–144 |
| 13 | —C(O)O—(n-C₃H₇) | 94–95 |
| 14 | —C(O)O—(n-C₅H₁₁) | 82–83 |
| 15 | —N(n-C₄H₉)C(O)O—CH₃ | 109–112 |
| 16 | —N(t-C₄H₉)C(O)O—(t-C₄H₉) | 80–82 |
| 17 | —N(CH₃)C(O)O—(i-C₃H₇) | 95–98 |
| 18 | —N(CH₃)C(O)O—(t-C₄H₉) | 122–124 |

EXAMPLES 19–30

By methods analogous to those described in Examples 1 to 3, further intermediates of the following formula were prepared, the identity and the melting point of each product being given in Table II. In each case, the identity of the product was confirmed by appropriate elemental and spectral analyses, and by identification of the product of Formula I prepared therefrom.

TABLE II

| Example No. | R | Melting Point (°C.) |
|---|---|---|
| 19 | —N(CH₃)C(O)O—CH₃ | 106–109 |
| 20 | —N(CH₃)C(O)O—(n-C₅H₁₁) | 74–76 |
| 21 | —N(C₂H₅)C(O)O—C₂H₅ | 76–78 |
| 22 | —N(t-C₄H₉)C(O)O—CH₃ | Not isolated |
| 23 | —N(t-C₄H₉)C(O)O—C₂H₅ | Not isolated |
| 24 | —N(n-C₄H₉)SO₂CH₃ | 97–98 |
| 25 | —C(O)O—(n-C₃H₇) | 61–62 |
| 26 | —C(O)O—(n-C₅H₁₁) | 54–55 |
| 27 | —N(n-C₄H₉)C(O)O—CH₃ | Brown oil |
| 28 | —N(t-C₄H₉)C(O)O—(t-C₄H₉) | Brown oil |
| 29 | —N(CH₃)C(O)O—(i-C₃H₇) | Brown oil |
| 30 | —N(CH₃)C(O)O—(t-C₄H₉) | Brown oil |

The following Examples further illustrate the invention, being drawn to the subgenus of formula I wherein at least one of X and X³ is fluorine; Examples 31 to 34 illustrate the preparatin of intermediates of Formula II, while Examples 35 to 38 illustrate the preparation of compounds of Formula I. As in the earlier examples, in each case the identity of the product was confirmed by appropriate elemental and spectral analyses.

EXAMPLE 31

2-fluoro-4-(2-chloro-4-[trifluoromethyl]phenoxy)aniline (31)

A solution of 7.1 g of 2-fluoro-4-hydroxyaniline and 3.7 g of potassium hydroxide (85% pure) in 25 ml of dimethylsulphoxide (DMSO) was heated to 80° C. and treated with a solution of 10.9 g of 1,2-dichloro-4-(trifluoromethyl)benzene in 10 ml of DMSO. The mixture was stirred at 90°–95° C. for 20 hours, after which it was diluted with a mixture of water and dichloromethane. The organic phase was dried (Na₂SO₄) and the solvent was evaporated. The residue was chromatographed over silica gel using a 4:1 v:v mixture of toluene and petroleum ether to give 31, as a yellow oil.

EXAMPLE 32

Propyl N-[[[4-[2-chloro-4-(trifluoromethyl)phenoxyl]-2-fluorophenyl]amino]thio]-N-methylcarbamate (32)

A solution of 12.1 g of propyl N-chlorosuphenyl-N-methylcarbamate in 20 ml of diethyl ether was added over 20 minutes to a stirred solution of 18.3 g of 31, and 7 g of triethylamine in 70 ml of the same solvent, the temperature of the mixture being maintained at 15°–20° C. with cooling. Stirring was continued at room temperature for a further 1½ hours. The reaction mixture was then diluted with 200 ml of diethyl ether, washed with water, dried and stripped of solvent. The residue was added to 100 ml of toluene, then the toluene was evaporated under reduced pressure to leave 32, in crude form as a pale brown oil.

EXAMPLE 33

N-[[[4-[2-chloro-4-(trifluoromethyl)phenoxy]-2-fluorophenyl]amino]thio]-N-methylbutanamide (33)

A solution of 11.3 g of sulphur dichloride in 40 ml of dichloromethane was added over 20 minutes to a solution of 10.1 g of N-methylbutanamide in 35 ml of the same solvent with stirring, the temperature of the mixture beiing maintained at 10° C. Stirring at this temperature was continued for a further 30 minutes, when a solution of 8.7 g of pyridine in 15 ml of dichloromethane was added. The mixture was then stirred and allowed to warm to room temperature over 2 hours, then filtered. The solvent was stripped from the filtrate and the residue was extracted with diethyl ether. After filtration, solvent removal and distillation, 12.1 g of the sulphenyl chloride precursor was obtained, as an oil, boiling point 82°–84° C. at 13 Torr. 4.4 g of this oil was dissolved in 10 ml of diethyl ether and the resulting solution was added over 20 minutes to a mixture of 7.6 g of the 31 and 2.7 g of triethylamine in 30 ml of diethyl ether. After stirring for 30 minutes at room temperature, 150 ml diethyl ether was added, the resultant solution was washed three times with water, dried, stripped of solvent and purified by chromatography over silica using dichloromethane as eluent, to give 33, as a brown oil.

EXAMPLE 34

N-[[[4-[2-chloro-4-(trifluoromethyl)phenoxy]-2-fluorophenyl]amino]thio]-L-proline, methyl ester (34)

A solution of 11.3 go of sulphur dichloride in 20 ml of dichloromethane was added at room temperature over 15 minutes to a stirred solution of 16.6 g of L-proline, methyl ester hydrochloride in 50 ml of the same solvent, following which a solution of 17.4 g of pyridine in 20 ml of the same solvent was added to the reaction mixture over 30 minutes. After stirring overnight, the mixture was diluted with 150 ml of diethyl ether, filtered, and stripped of solvent to leave 17.8 g of the crude product. 4.3 g of this product was dissolved in 10 ml of diethyl ether and added over 15 minutes at room temperature to a stirred mixture of 6.1 g of 31, 2.2 g of triethylamine and 50 ml of diethyl ether. After stirring at room temperature for 30 minutes, 250 ml of diethyl ether was added, and the mixture was washed with water, dried and stripped of solvent. The residue was chromatographed over silica using a mixture of diethyl ether and petroleum ether as eluent, to give 34, as a brown oil.

EXAMPLE 35

Propyl 4-[4-[2-chloro-4-(trifluoromethyl)phenoxy]-2-fluorophenyl]-7-(2,6-difluorophenyl)-2-methyl-5,7-dioxo-3-thia-2,4,6-triazaheptanoate (35)

A solution of 2.0 g of 2,6-difluorobenzoyl isocyanate in 10 ml of dry methylene chloride was added rapidly to a stirred solution of 4.5 g of 32 in 20 ml of the same solvent at room temperature. After stirring for 4 hours the solvent was removed under reduced pressure, and the residue was purified by chromatography twice on silica, using first methylene chloride and then diethyl ether as eluent. The product thus obtained was finally purified by crystallization from diethyl ether/light petroleum to give 35, as colourless crystals, m.p.: 98°–99° C.

EXAMPLE 36

N-[[[4-[2-chloro-4-(trifluoromethyl)phenoxy]-2-fluorophenyl][[(2,6-difluorobenzoyl)amino]carbonyl]amino]thio]-N-methylbutanamide (36)

A solution of 2.0 g of 2,6-difluorobenzoylisocyanate in 5 ml of a 1:1 v:v mixture of toluene and petroleum ether was added at room temperature over 30 minutes to a stirred solution of 4.4 g of 33 in 20 ml of the same solvent. After stirring at room temperature for 2 hours, the mixture was filtered, and the collected solid product was recrystallized from a mixture of diethyl ether and petroleum ether to give 36, as a white solid, m.p.: 136°–138° C.

EXAMPLE 37

N-[[[4-[2-chloro-4-(trifluoromethyl)phenoxy]-2-fluorophenyl][[(2,6-difluorobenzoyl)amino]carbonyl]amino]thio]-L-proline, methyl ester (37)

A solution of 2.8 g of 2,6-difluorobenzoylisocayanate in 10 ml of 1:1 v:v mixture of toluene and petroleum ether was added at room temperature over 30 minutes to a stirred solution of 6.5 g of 34 in 20 ml of the same solvent. After the mixture was stirred at room temperature for 3 hours, the solvent was stripped and the residue purified by chromatography over silica using dichloromethane as eluent, to give 37, as a white solid, m.p.: 65°–68° C.

EXAMPLE 38

N[[[4-[2-chloro-4-(trifluoromethyl)phenoxy]-2-fluorophenyl][[di(n-propyl)amino]thio]amino]carbonyl]-2,6-difluorobenzamide (38)

A solution of 7.1 g of 2-fluoro-4-hydroxyaniline and potassium hydroxide (3.7 g, 85% pure) in 25 ml of dimethylsulphoxide was heated to 80° C. and treated with a solution of 10.9 g of 1,2-dichloro-4-(trifluoromethyl)-benzene in 10 ml of dimethylsulphoxide. The mixture was stirred at 90°–95° C. for 20 hours, after which time it was diluted with a mixture of water and dichloromethane. The organic phase was dried over sodium sulphate and the solvent was evaporated. Chromatography of the residue over silica gel using a 4:1 v:v mixture of toluene and petroleum ether gave 1.1 g of 2-fluoro-4-(trifluoromethyl)phenoxy]aniline (38A), as a yellow oil.

22.7 g of sulphur dichloride in 100 ml of dichloromethane was cooled to $-5°$ C. and a solution of 17.4 g of pyridine in 50 ml of dichloromethane was added, over 30 minutes, while the temperature was maintained between $-5°$ and 0° C. The resulting solution was stirred for 15 minutes and a solution of 20.2 g of di(n-propyl)amine dissolved in 50 ml of dichloromethane was added, over 30 minutes, while the temperature was maintained between $-5°$ and 0° C. The resulting solution was stirred for 2 hours, while the temperature was allowed to rise to ambient. The solution was filtered and the solvent was evaporated. 150 ml of diethyl ether was added, the resulting solution was filtered, and the filtrate evaporated. Distillation of the residue gave di(n-propyl)aminosulphenyl chloride (38B), b.p.: 94°–5° C. at 15 Torr.

A solution of 3.7 g of 38B in 25 ml of diethyl ether was added, over 20 minutes at 15°–20° C., to a solution of 2.2 g of triethylamine and 6.1 g of 38A in 100 ml of diethyl ether. The resulting solution was stirred at ambient temperature for 3 hours. 100 ml of diethyl ether was added, the solution was washed with water, and dried. The solvent was removed by evaporation, and the product [4-[2-chloro-4-(trifluoromethyl)phenoxy]-2-fluorophenyl][[di(n-propyl)amino]thio]amine (38C), was used without further purification, as follows:

2.6 g of 2,6-difluorobenzoyl isocyanate in 15 ml of diethyl ether was added over 30 seconds to 5.4 g of 38C. The solution was stirred at ambient temperature for 2.5 hours after which a slight precipitate formed. 50 ml of petroleum ether was added, and the resulting suspension was cooled in a freezer (−5° to 0° C.) for 3 hours. The precipitate which formed was filtered off and recrystallised from a 1:1 v:v mixture of diethyl ether and petroleum ether, to give 2.3 g of 38, as white crystals, m.p.: 118°–121° C.

EXAMPLE 39

N[[[4-[2-chloro-4-(trifluoromethyl)phenyl]-2-fluorophenyl][[diisopropylamino]thio]amino]carbonyl]-2,6-difluorobezamide (39)

39 was prepared, as a white solid, m.p.: 147°–149° C. in a similar manner to (38). The intermediate compound, di(isopropyl)aminosulphenyl chloride, boiled at 92°–4° C. at 20 Torr.

EXAMPLE 40

N[[[4-[2-chloro-4-(trifluoromethyl)phenoxy]-2-fluorophenyl][[diethylamino]thio]amino]carbonyl]-2,6-difluorobenzamide (40)

40 was prepared, as a white solid, m.p.: 140°–142° C. in a similar manner to 38. The intermediate compound, diethylaminosulphenyl chloride boiled at 60°–62° C. at 11 Torr. The further intermediate compound, [4-[2-chloro-4-(trifluoromethyl)phenoxy)-2-fluorophenyl][-[diethylamino]thio]amine was isolated, as a solid, m.p.: 58°–60° C.

EXAMPLES 41–57

By methods analogous to those of Examples 35 to 40, further compounds of the following formula were prepared from the corresponding intermediates of Formula II, the identities of the moieties R, $X^1$, $X^2$ and $X^3$ and the melting point of each product being given in each case in Table III.

TABLE III

| Example No. | R | $X^1$ | $X^2$ | $X^3$ | Melting Point (°C.) |
|---|---|---|---|---|---|
| 41 | —N(t-$C_4H_9$)C(O)O—$C_2H_5$ | H | H | H | 96–98 |
| 42 | —N($CH_3$)C(O)O—(i-$C_3H_7$) | H | H | H | 82–85 |
| 43 | —N(n-$C_4H_9$)C(O)O—$CH_3$ | H | H | H | 116–118 |
| 44 | —N($CH_3$)C(O)O—(t-$C_4H_9$) | H | H | H | 115–117 |
| 45 | —N(i-$C_3H_7$)C(O)O—$CH_3$ | H | H | H | 99–101 |
| 46 | —N(i-$C_3H_7$)C(O)O—(n-$C_3H_7$) | H | H | H | 116–118 |
| 47 | —N($CH_3$)C(O)O—(n-$C_4H_9$) | H | H | H | 72–75 |
| 48 | —N($CH_3$)C(O)O—(n-$C_{10}H_{21}$) | H | H | H | Brown oil |
| 49 | —N($CH_3$)C(O)—$CH_3$ | H | H | H | 107–110 |
| 50 | —N($CH_3$)C(O)—(n-$C_5H_{11}$) | H | H | H | 116–118 |
| 51 | —N($CH_3$)C(O)—(t-$C_4H_9$) | H | H | H | 94–96 |
| 52 | —N($CH_3$)C(O)—(n-$C_{11}H_{23}$) | H | H | H | 62–65 |
| 53 | —N($CH_3$)C(O)O—$C_2H_5$ | H | H | H | 104–106 |
| 54 | —N(i-$C_3H_7$)C(O)—(n-$C_3H_7$) | H | H | H | 56–59 |
| 55 | —N(t-$C_4H_9$)C(O)—(n-$C_3H_7$) | H | H | H | 116–118 |
| 56 | —1-(piperidyl) | H | H | H | 121–123 |
| 57 | —1-(2-(ethoxycarbonyl)piperidyl) | H | H | H | 77–80 |

EXAMPLES 58 TO 77

By methods analogous to those described in Examples 1 to 4, 31 to 34, and 38, further intermediates of formula below were prepared, the identity of moiety R and melting point of each product being given in Table IV. In each case, the identity of the product was confirmed by appropriate elemental and spectral analyses, and by identification of the product of Formula I prepared therefrom.

TABLE IV

| Example No. | R | Melting Point (°C.) |
|---|---|---|
| 58 | —N($CH_3$)C(O)(O—$C_2H_5$) | |
| 59 | —N(i-$C_3H_7$)C(O)—(n-$C_3H_7$) | |
| 60 | —N(t-$C_4H_9$)C(O)—(n-$C_3H_7$) | |
| 61 | —1-piperidyl | 94–96 |
| 62 | —N($C_2H_5$)$_2$ | 58–60 |
| 63 | —N(i-$C_3H_7$)$_2$ | |
| 64 | —N(n-$C_3H_7$)$_2$ | |
| 65 | —1-(2-(ethoxycarbonyl)piperidyl) | |
| 66 | —N($CH_3$)C(O)O—(i-$C_3H_7$) | |
| 67 | —N(n-$C_4H_9$)C(O)O—$CH_3$ | Brown oil |
| 68 | —N($CH_3$)C(O)O—(t-$C_4H_9$) | Brown oil |
| 69 | —N(n-$C_3H_7$)C(O)O—$CH_3$ | Brown oil |
| 70 | —N(i-$C_3H_7$)C(O)O—(n-$C_3H_7$) | Brown oil |
| 71 | —N($CH_3$)C(O)O—(n-$C_4H_9$) | Brown oil |
| 72 | —N($CH_3$)C(O)O—(n-$C_{10}H_{21}$) | Brown oil |
| 73 | —N($CH_3$)C(O)—$CH_3$ | Brown oil |
| 74 | —N($CH_3$)C(O)—(n-$C_5H_{11}$) | Brown oil |
| 75 | —N($CH_3$)C(O)—(t-$C_4H_9$) | Brown oil |
| 76 | —N($CH_3$)C(O)—(n-$C_{11}H_{23}$) | Brown oil |
| 77 | —N(t-$C_4H_9$)C(O)O—$C_2H_5$ | Pale brown oil |

EXAMPLE 78

Insecticidal Activity

The insecticidal activity of the compounds of the invention was determined in the following tests, employing the pests Spodoptera littoralis (S.l.) and Aedes aegypti (A.a.).

The test methods used for each species appear below. In each case the tests were conducted under normal conditions (23° C.±2° C.; fluctuating light and humidity).

In each test an $LC_{50}$ (the dosage of active material required to kill half of the test species) for the compound was calculated from the mortality figures and compared with the corresponding $LC_{50}$ for a standard insecticide, ethyl parathion, in the same tests. The results are expressed as toxicity indices thus:

$$\text{toxicity index} = \frac{LC_{50} \text{ (parathion)}}{LC_{50} \text{ (test compound)}} \times 100$$

and are set out in Table III below.

(i) Spodoptera littoralis

Solutions or suspensions of the compound were made up over a range of concentrations in 10% acetone/water containing 0.025% Triton X 100 ("Triton" is a registered trademark). These solutions were sprayed using a logarithmic spraying machine onto petri dishes containing a nutritious diet on which the Spodoptera littoralis larvae had been reared. When the spray deposit had dried each dish was infested with 10 2nd instar larvae. Mortality assessments were made 7 days after spraying.

(ii) Aedes aegypti

Several solutions of the test compound of varying concentration were prepared in acetone. 100 microliter quantities were added to 100 milliliters of tap water, the acetone being allowed to evaporate. 10 early 4th instar larvae were placed in the test solution; after 48 hours the (surviving) larvae were fed with animal feed pellets, and the final percentage mortality assessed when all the larvae had either pupated and emerged as adults or died. The results are set out in Table V.

TABLE V

| | Insecticidal Activity | |
|---|---|---|
| | Toxicity Index (TI) | |
| Compound of Example No. | S.l. | A.a. |
| 4 | 2900 | 600 |
| 5 | 3900 | 850 |
| 6 | 1100 | 190 |
| 7 | 4100 | 990 |
| 8 | 4000 | 860 |
| 9 | 4100 | 680 |
| 10 | 3700 | 630 |
| 11 | 2400 | 650 |
| 12 | 3900 | 850 |
| 13 | 2000 | 310 |
| 14 | 2100 | 120 |
| 15 | 5800 | 740 |
| 16 | 7300 | 820 |
| 17 | 4200 | 930 |
| 18 | 3400 | 850 |
| 35 | 2800 | 790 |
| 36 | 1500 | 880 |
| 37 | 2700 | 1300 |
| 38 | 3300 | 920 |
| 39 | 4900 | 490 |
| 40 | 1800 | 1600 |
| 41 | 5500 | 620 |
| 42 | 5200 | 1290 |
| 43 | 6300 | 810 |
| 44 | 3000 | 950 |
| 45 | 6230 | 1370 |
| 46 | 4360 | 940 |
| 47 | 1840 | 570 |
| 48 | 2860 | 1100 |
| 49 | 2000 | 470 |
| 50 | 2100 | 530 |
| 51 | 3000 | 610 |
| 52 | 2000 | 1200 |
| 53 | 1900 | 840 |
| 54 | 4400 | 1000 |
| 55 | 1900 | 680 |
| 56 | 1500 | 1600 |
| 57 | 6100 | 650 |

EXAMPLE 79

Acaricidal Activity

Leaf discs were infested with 30–60 larvae of the mite *Tetranuchus urticae* and sprayed with varying dosages of solutions of the test compounds made up as in test (i) of Example 78 above. When dry, the discs were maintained at constant temperature for 12 days, after which mortality assessments were made, and the $LC_{50}$ values calculated. The results are set forth in Table VI.

TABLE VI

| | Acaricidal Activity |
|---|---|
| Compound of Example No. | $LC_{50}$ (% active ingredient in spray) |
| 4 | 0.00027 |
| 5 | 0.00020 |
| 6 | 0.0010 |
| 7 | 0.00018 |
| 8 | 0.00017 |
| 9 | 0.00027 |
| 10 | 0.00022 |
| 11 | 0.00032 |

TABLE VI-continued

| | Acaricidal Activity |
|---|---|
| Compound of Example No. | $LC_{50}$ (% active ingredient in spray) |
| 12 | 0.00015 |
| 13 | 0.0030 |
| 14 | 0.00073 |
| 15 | 0.00016 |
| 16 | 0.00014 |
| 17 | 0.000096 |
| 18 | 0.00014 |
| 35 | 0.00025 |
| 36 | 0.00015 |
| 41 | 0.00038 |
| 42 | 0.00028 |
| 43 | 0.00021 |
| 44 | 0.00028 |
| 45 | 0.00018 |
| 46 | 0.00029 |
| 47 | 0.00015 |
| 48 | Not tested |
| 49 | Not tested |
| 50 | Not tested |
| 51 | 0.00010 |
| 52 | Not tested |

We claim:

1. A compound of the formula:

[Chemical structure: a fluorinated phenyl group with substituent A, connected via –C(O)–N(H)–C(O)–N(R)(S)– to a phenyl ring bearing X, $X^1$, $X^2$, $X^3$ substituents, linked by –O– to another phenyl ring with Cl and $CF_3$ substituents]

wherein A is fluorine or chlorine, X, $X^1$, $X^2$ and $X^3$ each is hydrogen or fluorine, R is a moiety —C(O)O$R^1$, or —N$R^2R^3$, in which $R^1$ and $R^2$ each is optionally substituted alkyl, optionally substituted cycloalkyl or optionally substituted phenyl, $R^3$ is optionally substituted alkyl, optionally substituted cycloalkyl optionally substituted phenyl, or is a moiety —C(O)$R^4$, —C(O)O$R^4$ or —SO$_2R^4$ wherein $R^4$ is optionally substituted alkyl, optionally substituted cycloalkyl or optionally substituted phenyl, or $R^2$ and $R^3$ together is optionally substituted alkylene of four or five carbon atoms, in each case the optional substituents on alkyl, cycloalkyl and alkylene being selected from halogen, alkoxy, alkoxycarbonyl, haloalkoxycarbonyl, alkylcarbonyl, haloalkylcarbonyl, alkylsulphonyl and haloalkysulphonyl, and the optional substituents on phenyl being selected from these substitutents and also alkyl, haloalkyl, cyano and nitro, wherein each alkyl and haloalkyl group contains from one to six carbon atoms.

2. A compound according to claim 1 wherein R is —N$R^2R^3$ wherein $R^2$ is alkyl and $R^3$ is alkyl or a group of the formula —C(O)O$R^4$, —SO$_2R^4$ or —C(O)$R^4$ wherein $R^4$ is alkyl.

3. A compound according to claim 2 wherein A is fluorine.

4. A compound according to claim 3 wherein each of X, $X^1$, $X^2$ and $X^3$ is hydrogen.

5. A compound according to claim 3 wherein X is fluorine and each of $X^1$, $X^2$ and $X^3$ is hydrogen.

6. An insecticidal/acaricidal composition comprising an effective amount of a compound of claim 1 together with at least two carriers, one of which is a surface-active agent.

7. An insecticidal/acaricidal composition comprising an effective amount of a compound of claim 2 together with at least two carriers, one of which is a surface-active agent.

8. An insecticidal/acaricidal composition comprising an effective amount of a compound of claim 3 together with at least two carriers, one of which is a surface-active agent.

9. An insecticidal/acaricidal composition comprising an effective amount of a compound of claim 4 together with at least two carriers, one of which is a surface-active agent.

10. An insecticidal/acaricidal composition comprising an effective amount of a compound of claim 5 together with at least two carriers, one of which is a surface-active agent.

11. A method for for combating insects and/or mites at a locus that comprises applying to the locus an effective dosage of a compound of claim 1.

12. A method for for combating insects and/or mites at a locus that comprises applying to the locus an effective dosage of a compound of claim 2.

13. A method for for combating insects and/or mites at a locus that comprises applying to the locus an effective dosage of a compound of claim 3.

14. A method for for combating insects and/or mites at a locus that comprises applying to the locus an effective dosage of a compound of claim 4.

15. A method for for combating insects and/or mites at a locus that comprises applying to the locus an effective dosage of a compound of claim 4.

* * * * *